United States Patent [19]
Willits et al.

[11] Patent Number: 4,764,115
[45] Date of Patent: Aug. 16, 1988

[54] PARTIAL DENTURE WITH INTEGRALLY FORMED ELASTIC RETAINER STRIP

[75] Inventors: William G. Willits; Thomas T. Schmitt, both of Norfolk, Va.

[73] Assignee: Denture Clinic, Inc., Norfolk, Va.

[21] Appl. No.: 7,768

[22] Filed: Jan. 28, 1987

[51] Int. Cl.[4] ............................................. A01C 13/22
[52] U.S. Cl. ..................................... 433/177; 433/172
[58] Field of Search ............... 433/167, 168, 172, 177, 433/6

[56] References Cited

U.S. PATENT DOCUMENTS

| 4,253,828 | 3/1981 | Coles et al. | 433/6 |
| 4,514,173 | 4/1985 | Re | 433/178 |

Primary Examiner—Robert Peshock
Attorney, Agent, or Firm—Rhodes, Coats & Bennett

[57] ABSTRACT

The present invention entails a partial denture formed of a relatively hard acrylic material. Molded into a selected portion of the denture is an area of relatively soft material. A teeth opening is formed in the soft material, the opening being at least slightly elongated to receive at least two successive existing teeth of the subject. Forming a part of the soft material and the existing teeth opening is an elastic retainer strip that engages the gum area of the subject adjacent the existing teeth. The elastic retainer strip engages or grips the subject's gum, resulting in the partial denture being secured within the subject's mouth.

13 Claims, 2 Drawing Sheets

PARTIAL DENTURE WITH INTEGRALLY FORMED ELASTIC RETAINER STRIP

FIELD OF INVENTION

The present invention relates to denistry and partial dentures, and more particularly to retaining devices and structures for retaining partial dentures in a subject's mouth.

BACKGROUND OF THE INVENTION

There are two conventional ways to retain partial dentures. In clasp type attachments or direct retainers, metal retentive clasps are formed in the base of the denture. The clasps snap downwardly over selected teeth and engage the undercut area of the tooth.

There are numerous drawbacks to clasp type partial dentures. First, clasp type partial dentures require the presence of strong teeth since they place great stress on teeth to which the clasps are secured. The clasps cannot be secured to weak or questionable teeth. Secondly, the retentive clasps can be irritating or uncomfortable to the denture wearer making their use an unattractive alternative.

Precision retainers are also commonly used to secure partial dentures. Precision retainers employ snap connectors secured to an existing tooth structure by means of a cap, bridge, etc. A mating connector is formed into the base of the partial denture. As with clasp type partial dentures, precision retainers require the presence of strong teeth. Additionally, partial dentures with precision retainers are relatively expensive.

A more unconventional approach for retaining partial dentures is also known. An opening is formed in the denture base through which a single existing tooth projects. The opening is lined with a soft material that engages the individual tooth to hold the partial denture in place.

SUMMARY AND OBJECTS OF THE INVENTION

The present invention provides a partial denture and means for retaining the same that overcomes the disadvantage of prior art partial dentures. In particular, the partial denture of the present invention includes a base formed of hard acrylic having buccal and lingual flanges. A portion of the buccal flange adjacent the position of existing teeth is removed and partially replaced by a soft silicone based material so that an elongated opening is formed through which existing teeth extend. The silicone portion of the buccal flange forms an elastic retainer that engages the receeding area below the lower teeth. Thus, the partial denture of the present invention is tissue supported and is suitable for use with even weak teeth which might otherwise be removed if other retaining means were used.

The primary object of the present invention is to provide a partial denture and retaining means therefor which can be used in connection with weak or questionable teeth so that they need not be removed.

Another object of the present invention is to provide a partial denture that is extremely flexible and can receive virtually any tooth configuration.

Another object of the present invention is to provide a partial denture that is soft, thin and comfortable to the denture wearer.

Another object of the present invention is to provide a partial denture that eliminates stress placed on existing teeth by prior art dentures.

Another object of the present invention is to provide a partial denture that permits slight movement of the denture while chewing to reduce stress placed on existing teeth.

Still another object of the present invention is to provide a partial denture that is tissue supported rather than being supported by snaps or clasps that engage existing teeth.

Another object of the present invention is to provide a partial denture that incorporates an elastic retainer that engages the recessed area beneath the lower teeth.

Other objects and advantages of the present invention will become apparent and obvious from a study of the following description and the accompanying drawings which are merely illustrative of such invention.

PARTIAL DENTURE WITH INTEGRALLY FORMED ELASTIC RETAINER STRIP

Figure 1:
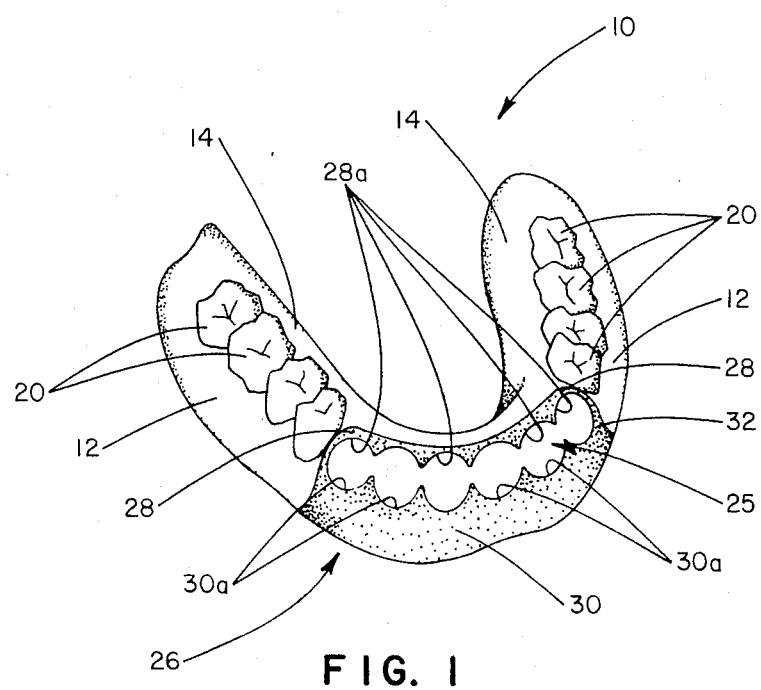
FIG. 1 is a perspective view of the partial denture of the present invention constructed in accordance with the present invention.

With further reference to the drawings, the partial denture of the present invention is shown therein and indicated generally by the numeral 10.

Partial denture 10 comprises a base denture molded in conventional fashion from a conventional denture material, typically a relatively hard acrylic material or other conventional material used in the industry. The base denture structure includes a front buccal flange 12 and rear lingual flange 14. Buccal and lingual flanges 12 and 14 are integrally molded together to form a ridge 16 that extends in a horseshoe or U-shaped fashion around the denture 10. It is appreciated that the buccal and lingual flanges 12 and 14 combine with ridge 16 to form a gum cavity 18 that is particularly shaped to receive the subject's gum structure.

Artifical teeth 20 is secured along ridge 16 in the area where the patient or subject has missing teeth. In the case of the partial denture disclosed herein, the particular subject for whom the denture is designed has a series of six existing teeth 21 that will be received and accommodated by the partial denture 10. To provide accommodations for existing teeth 21, the base denture structure includes an existing teeth opening indicated in FIG. 1 generally by the reference numeral 25. Existing teeth opening 25 is an elongated opening as it is of a length sufficient to receive at least two successive existing teeth of the patient or subject.

The present invention relates to retaining partial denture 10 in the patient's mouth about the existing teeth 21 extending through the existing teeth opening 25. As noted above, the basic denture supporting artificial teeth 20 is molded from a conventional relatively hard acrylic denture material. Details of such are not dealt with herein because such is not per se material to the present invention and because such materials are well known and appreciated in the denture art.

Figure 2:
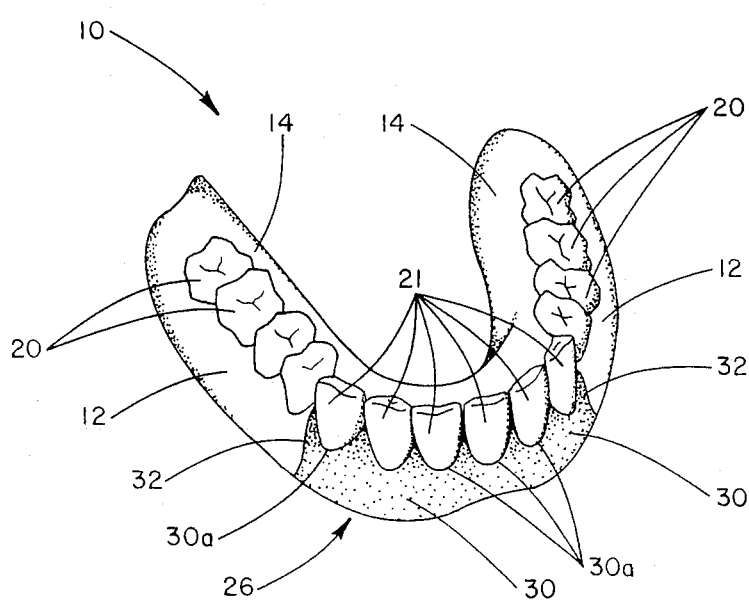
FIG. 2 is another perspective view of the partial denture of the present invention illustrating the partial denture disposed in a subject's teeth.

But surrounding the existing teeth opening 25 and formed along the adjacent buccal flange areas is a relatively soft acrylic material area 26 that joins with and is integrally molded with the hard acrylic material (FIG. 2).

Figure 3:
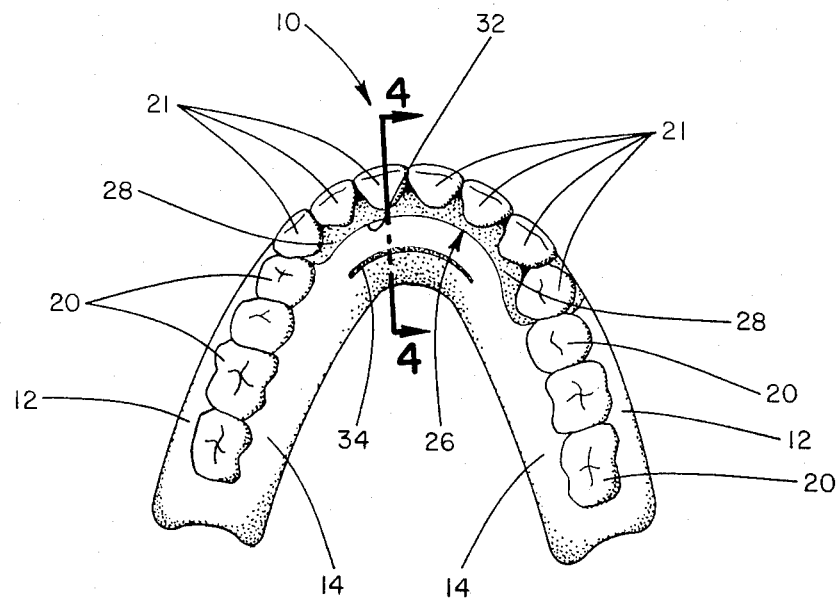
FIG. 3 is also a perspective view of the partial denture of the present invention as viewed from a rear perspective to better illustrate the lingual flange.

Viewing the relatively soft acrylic material area 26 in detail, first note there is provided a thin strip of this soft acrylic material along the back side and opposite ends of the existing teeth opening 25. This thin strip of material is indicated by the numeral 28 and is best shown and illustrated in FIG. 3. In particular, the thin strip of soft acrylic material 28 effectively lines the side and ends of the existing teeth opening 25 that lies adjacent the lingual flange 14. Note also in FIG. 1 that the thin strip of soft acrylic material 28 is particularly shaped with undercut indentions 28a that are in an arcuate or U-shape. These undercut indentions 28a allow the backside of existing teeth opening 25 to engage an undercut area that typically exists in the area where the existing teeth emerge from the patient's or subject's gum area. As will be more fully appreciated from subsequent portions of this disclosure, these undercut indentions 28a will engage the undercut areas of the existing teeth in such a manner that they will contribute to the retention of the partial denture 10 in the patient's mouth.

Continuing to refer to the relatively soft material area 26 surrounding the existing teeth opening 25, it is seen that there is provided an elastic retainer strip 30 that extends horizontally across a selected portion of the buccal flange 12. Elastic retainer strip 30, as seen in FIGS. 1 and 2, extend along and adjacent the existing teeth opening 25 and includes an inner edge that actually forms a part of the border of the existing teeth opening 25. As was the case with the thin strip 28 formed on the backside of the existing teeth 25, the inner edge of the elastic retainer strip 30 also includes a series of undercut indentions 30a. These undercut indentions 30a are shaped and designed to fit into the undercut areas of the patient's or subject's existing teeth about the front area thereof, as illustrated in FIG. 2.

Figure 4:
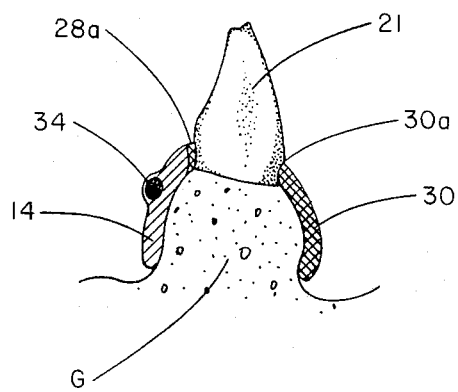
FIG. 4 is a cross sectional view taken through the lines 4—4 of FIG. 3.

Elastic retainer strip 30 serves to actually retain partial denture 10 in the subject's mouth. It is important that the elastic retainer strip 30 be elastic, pliable, and stretchable. These qualities and characteristics allow the elastic retainer strip 30 to stretch over the existing teeth when the partial denture 10 is being installed and once the denture assumes an appropriate position on the patient's gums G (FIG. 4), then the undercut indentions 30a project into and lie in the undercut areas of the existing teeth that are formed along the gum line where the existing teeth emerge from the gum G. In addition, the elastic nature of the retainer strip 30 is such that the elastic retainer strip 30 is gently but firmly pulled against the gum area G (FIG. 4) extending underneath the existing teeth 21 and that serves to retain and secure the partial denture 10 in the subject's mouth. It should be pointed out that the thin strip of soft acrylic material 28a that extends around the existing teeth opening 25 opposite the elastic retainer strip 30 provides a soft interface between the denture 10 and the subject's teeth and gums. This clearly makes for a comfortable fitting denture.

As illustrated in the drawings, the relatively soft acrylic material just described and surrounding the existing teeth opening 25 is integrally molded to the hard acrylic material that surrounds and supports the artificial teeth 20.

In producing the present partial denture, the complete denture base including a continuous buccal flange is formed for the particular patient's mouth by a conventional denture molding process.

Figure 5:
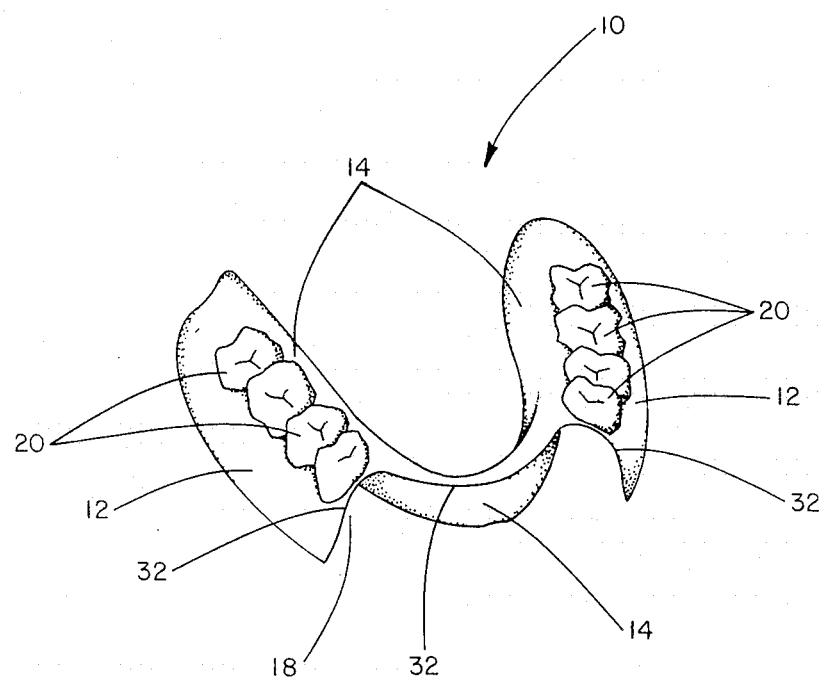
FIG. 5 is a perspective view of the partial denture of the present invention after an initial molding process and after an area has been cut therefrom to accept the relatively soft material that forms the elastic retainer strip and which generally surrounds the existing teeth opening.

Once the base denture 10 has been produced with the hard acrylic material, then an area is cut from the base denture structure as partially shown in FIG. 5. This cut area is generally that area referred to above or the soft material area 26 and bounded by the transitional line 32 shown in FIGS. 1, 2, 3, and 5. Effectively, that portion of the denture represented by the soft acrylic material 26 is cut from the original denture base made from the relatively hard acrylic material. After removing that portion of the original denture base, the cut denture shown in FIG. 5 is again placed over the patient's master mold which includes a mold of his or her existing teeth. Then the relatively soft acrylic material is poured over the master mold and around the mold representations of the patient's existing teeth. Once the relatively soft acrylic material is poured, the denture is then exposed to a second molding process. Here the relatively soft acrylic material is integrally molded with the relatively hard acrylic material that forms the remaining part of the partial denture 10. Once this second molding process is completed and the finishing work has been done, the produced partial denture 10 then assumes a construction and design such as discussed above and shown in FIGS. 1, 2 and 3.

The relatively soft material 26 used about the existing teeth opening 25 is of the type known as "molloplast-B" produced by Molloplast.Regneri and Co. KG, Karlsruhe, West Germany. This material is a permanently soft silicone based refining material especially developed for prosthetic dentistry. It is appreciated that other types of such materials may be used in and around the existing teeth opening 25 of the partial denture 10 to provide such a retention structure.

To provide additional support to the partial denture 10, the same may be provided with a reinforcing wire strip 34 integrally molded into the partial denture about the lingual flange 14 opposite the area occupied by the elastic retainer strip 30.

From the foregoing specification and discussion, it is appreciated that the partial denture 10 of the present invention includes many advantages over the clasp type and precision attachment partial dentures. Foremost, it enables the patient to retain as many of his or her permanent teeth as possible. Because the teeth themselves are not directly engaged by the retention of the partial denture, then this means that even a questionable or marginal tooth can be maintained and not extracted. Moreover, the soft silicone based material 26 forms a soft interface about the patient's gum area. This avoids irritation and discomfort that is commonly found in and around the existing teeth. Also the total design of the partial denture allows the same to be at least slightly mobile in the patient's mouth. This mobility while chewing prevents the denture from exerting substantial pressure and stress against the patient's or subject's existing teeth. Beyond the above, the partial denture of the present invention is not unduly expensive but is simple and affordable.

The present invention may, of course, be carried out in other specific ways than those herein set forth without parting from the spirit and essential characteristics of the invention. The present embodiments are, therefore, to be considered in all respects as illustrative and not restrictive, and all changes coming within the meaning and equivalency range of the appended Claims are intended to be embraced therein.

What is claimed is:

1. A partial denture comprising: a denture base including buccal and lingual flanges molded of a relatively hard material and shaped to form a ridge for supporting a selective number of artificial teeth; an opening formed in the ridge with the opening being at least large enough to receive a plurality of successive existing teeth of the subject; and elastic material surrounding the opening for receiving existing including an elastic retainer strip forming a part of the denture base and extending along one side of said elongated teeth opening for engaging the subject's gum area adjacent the subject's existing teeth extending upwardly through the teeth opening and for securing the partial denture within the subject's mouth due to the engagement of the elastic retainer strip with that gum area, whereby the elastic material tends to form a cushion around the existing teeth and the elastic retainer strip acts to secure and hold the partial denture in the subject's mouth.

2. The partial denture of claim 1 wherein said existing teeth opening for receiving the subject's existing teeth is elongated and includes opposite ends and wherein the elastic retainer strip extends between the opposite end of the elongated opening in such a fashion that one edge of the elastic strip forms an edge of the elongated teeth opening.

3. The partial denture of claim 2 wherein said buccal and lingual flanges include a terminal edge opposite the ridge, and wherein the elastic retainer strip forms a part of a respective flange and includes an outer terminal edge, opposite the inner edge, that aligns with the terminal edge of the respective flange in which it forms a part.

4. The partial denture of claim 1 wherein the denture base is molded and a voided area is formed in the relatively hard material about one flange area adjacent said elongated tooth opening; and wherein said voided area includes two laterally spaced apart terminal edges formed of the relatively hard material; and wherein said elastic retainer strip is integrally molded with said terminal edges of the voided area such that the elastic retainer strip actually spans the voided area and wherein the elastic retainer strip includes an inner edge that forms a portion of the elongated teeth opening.

5. The partial denture of claim 1 wherein there exists an undercut area that lies along a gum line where the subject's existing teeth emerge from the gum, and wherein said elastic retainer strip includes an engaging inner edge that forms a part of said tooth opening and which generally engages the undercut area so as to form a secure relationship between the subject's existing teeth and the teeth opening.

6. A partial denture with a relatively soft elastic retainer strip integrally formed therein for engaging an area of subject's gum and retaining the partial denture in the subject's mouth, comprising: a partial denture formed of a relatively hard material having a pair of flanges that form a ridge and which together form a gum cavity for receiving the subject's gum; an opening formed in the ridge area of the partial denture with a width sufficient to receive at least two successive existing and standing teeth of the subject; an area of relatively soft material formed about and around said opening for forming a comfortable interface between the denture opening and the subject's existing teeth and gum and including strip formed of a relatively soft material and integrally formed in the partial denture for engaging the gum area adjacent existing teeth of the subject and securing the denture within the subject's mouth; said elastic retainer strip forming a part of the opening for receiving existing teeth and extending along one side of the opening; and wherein said elastic retainer strip normally assumes a retentive position along a gum area adjacent the existing teeth and actually engages the gum whereby the retentive action of the elastic retainer strip against the gum assures that the denture is held within the subject's mouth.

7. The partial denture of claim 6 wherein the elastic retainer strip extends horizontally along a gum area above or below the existing teeth, depending on whether the partial denture is an upper or lower denture.

8. The partial denture of claim 7 wherein the elastic retainer strip includes an inner edge that forms a segment of the opening for existing teeth and wherein the inner edge is particularly shaped to lie in an undercut area defined about the front of the gum where the existing teeth emerge from the gum and wherein the engagement of the inner edge of the elastic retainer strip with the undercut area assures a relatively firm connection between the partial denture and the subject's mouth.

9. The partial denture of claim 6 wherein the front flange of the denture is referred to as buccal flange and wherein the buccal flange is formed of the relatively hard material and is provided with a voided area extending adjacent the existing teeth opening on the ridge with the voided area being bounded by two laterally spaced terminal edges; and wherein said elastic retainer strip is molded to the buccal flange and extends from one terminal edge to the other and across the defined voided area; and wherein the elastic retainer strip includes an inner edge and forms a part of the existing opening.

10. The partial denture of claim 6 wherein the denture is provided with a wire reinforcing strip integrally formed in the flange opposite the elastic retainer strip.

11. A method of forming a partial denture comprising the steps of: molding a denture of relatively hard material for a particular subject's mouth such that the denture includes both a buccal and lingual flange and an upper ridge; cutting an elongated opening in the ridge so as to form a teeth receiving opening and wherein the opening is of sufficient width to receive a pluraltiy of successive existing teeth of the subject; cutting the buccal flange and forming a voided area adjacent the existing teeth opening so as to form one large opening that comprises the existing teeth opening and the cut voided area; molding a relatively soft material around the formed existing teeth opening including molding an elastic retainer strip to the buccal flange and extending the elastic retaining strip over the cut voided area formed in the buccal flange such that the existing teeth opening is now bound along one side by the elastic retaining strip whereby the elastic retainer strip engages the subject's gum area underlying the subject's existing teeth and secures the partial denture in the subject's mouth.

12. The method of claim 11 including the step of molding a wire reinforcing strip into the lingual flange opposite the area now occupied by the elastic retaining strip.

13. The method of claim 12 including the step of shaping an inner edge of the elastic retainer strip, the inner edge being that edge that forms a part of the existing teeth opening; and wherein the step of shaping the inner edge includes the inner edge to fit and extend across an undercut area of the patient's existing teeth which are to extend through the existing teeth opening of the denture.

* * * * *